(12) United States Patent
Nicholson, IV

(10) Patent No.: US 7,566,298 B2
(45) Date of Patent: Jul. 28, 2009

(54) METHOD OF AND APPARATUS FOR PREVENTION OF ADJUSTABLE GASTRIC BAND SLIPS

(76) Inventor: William Daniel Nicholson, IV, 12215 Park Forest, Dallas, TX (US) 75230

( * ) Notice: Subject to any disclaimer, the term of this patent is extended or adjusted under 35 U.S.C. 154(b) by 160 days.

(21) Appl. No.: 11/421,946

(22) Filed: Jun. 2, 2006

(65) Prior Publication Data

US 2007/0249894 A1  Oct. 25, 2007

Related U.S. Application Data

(60) Provisional application No. 60/745,584, filed on Apr. 25, 2006.

(51) Int. Cl.
*A61F 2/00* (2006.01)
(52) U.S. Cl. ...................................................... 600/37
(58) Field of Classification Search .................. 600/37, 600/29–32; 606/151
See application file for complete search history.

(56) References Cited

U.S. PATENT DOCUMENTS

| 4,551,862 | A | * | 11/1985 | Haber | 600/30 |
| 5,074,868 | A | * | 12/1991 | Kuzmak | 606/157 |
| 5,259,846 | A | * | 11/1993 | Granger et al. | 606/224 |
| 6,432,040 | B1 | * | 8/2002 | Meah | 600/37 |
| 2006/0252983 | A1 | * | 11/2006 | Lembo et al. | 600/37 |
| 2007/0016231 | A1 | * | 1/2007 | Jambor et al. | 606/157 |

OTHER PUBLICATIONS

Intragastric Band Erosion After Laparoscopic Adjustable Gastric Banding for Morbid Obesity: Imaging Characteristics of an Underreported Complication by Bernard Hainaux, et al.; American Journal of Roentgenology 2005; 184:109-112.
Complications of Adjustable Gastric Banding, a Radiological Pictorial Review by Mayssoun J. Mehanna, et al.; American Journal of Roentgenology 2006; 186:522-534.

\* cited by examiner

*Primary Examiner*—Samuel G Gilbert
(74) *Attorney, Agent, or Firm*—Michael A. O'Neil (57) ABSTRACT

A gastric restrictive device positionable around a human stomach to limit the flow of food therethrough is provided with structure for facilitating suturing of the gastric restrictive device to the stomach and thereby preventing movement of the gastric restrictive device relative to the stomach.

7 Claims, 6 Drawing Sheets

METHOD OF AND APPARATUS FOR PREVENTION OF ADJUSTABLE GASTRIC BAND SLIPS

CROSS-REFERENCE TO RELATED APPLICATIONS

Applicant claims priority based on provisional patent application Ser. No. 60/745,584 filed Apr. 25, 2006, the entire content of which is incorporated herein by reference.

TECHNICAL FIELD

This invention relates generally to the treatment of morbid obesity by means of adjustable gastric bands, and more particularly to a method of and apparatus for preventing gastric band slips during the treatment procedure.

BACKGROUND AND SUMMARY OF THE INVENTION

Figure 1:
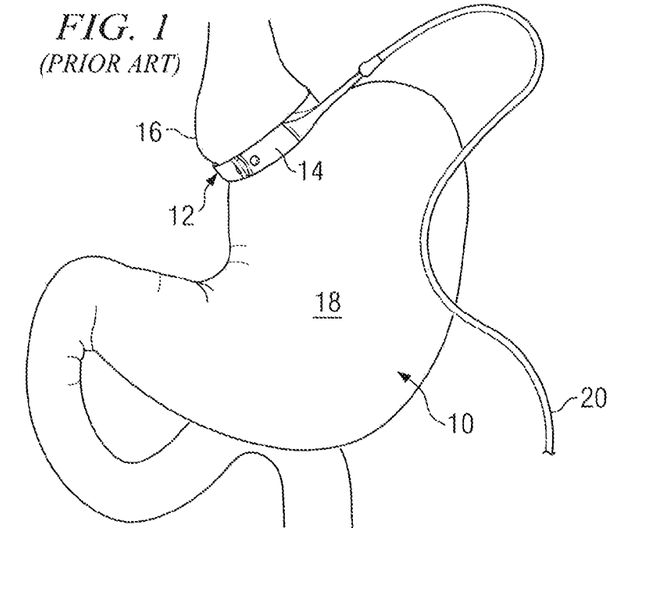
FIG. 1 is an illustration of an adjustable gastric band properly installed on a stomach.

Referring to the Drawings, and particularly to FIG. 1 thereof, there is shown a human stomach 10 having an adjustable gastric band 12 secured therearound. As is well known to those skilled in the art, the adjustable gastric band 12 typically includes an outer flexible, substantially non-extendable layer 14 and an inner expandable layer which is secured to the outer layer 14.

In use, the adjustable gastric band 12 is extended around the stomach 10 at the location shown in FIG. 1. The adjustable gastric band 12 is then secured in place by joining the opposite ends of the flexible, substantially non-extendable layer 14 utilizing a latch. When the adjustable gastric band 12 is thus secured in place the stomach is divided into a relatively small upper portion 16 and a relatively larger lower portion 18.

The adjustable gastric band 12 is provided with a tube 20 which extends through an incision made in the abdominal wall of the patient to a location outside of the abdominal cavity. Sterile saline is directed through the tube 20, through a valve, and into the expandable inner layer of the adjustable gastric band 12 thereby causing the expandable inner layer to balloon inwardly. In this manner the passage of food from the upper portion 16 to the lower portion 18 of the stomach 10 is restricted.

It is theorized that the upper portion 16 of the stomach 10 and/or the adjacent lower region of the esophagus contains nerve endings which trigger a "full" feeling when the stomach 10 is full. When the adjustable gastric band 12 is positioned as illustrated in FIG. 1 and when the flexible inner wall of the adjustable gastric band is inflated, food accumulates in the upper portion 16 and in the adjacent lower region of the esophagus. This causes the patient to experience a "full" feeling even though the lower portion 18 of the stomach 10 is in fact not full. Because the patient experiences a "full" feeling after consuming a relatively small amount of food the patient's total caloric intake is reduced thereby facilitating control of the patient's obesity. As is understood by those skilled in the art, the inner flexible layer of the adjustable gastric band 12 is further expanded as the obesity treatment progresses thereby further restricting the passage of food from the upper portion 16 to the lower portion 18 of the stomach 10.

Figure 2:
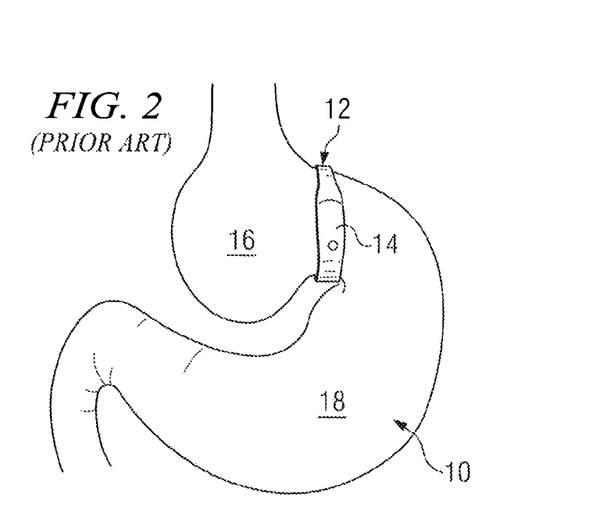
FIG. 2 is an illustration of an adjustable gastric band slip.

In between about 3% and about 5% of the 40,000+ cases annually in which an adjustable gastric band is used in the treatment of morbid obesity the adjustable gastric band 12 moves downwardly relative to the stomach 10, an occurrence known as a slip. When an anterior slip occurs the adjustable gastric band moves into the improper vertical orientation illustrated in FIG. 2 as opposed to the proper angular orientation illustrated in FIG. 1. A slip of the type illustrated in FIG. 2 is dangerous because it results in food accumulating in the upper portion 16 of the stomach 10 rather than flowing smoothly from the upper portion 16 to the lower portion 18 of the stomach 10 albeit at a slower than normal rate. Accumulation of food in the upper portion 16 of the stomach 10 can cause the patient to experienced frequent vomiting. More importantly, a slip directly restricts blood flow to the herniated portion of the stomach which can cause necrosis thereof which can lead to a surgical emergency and possibly death.

As is also well known to those skilled in the art a posterior slip of the adjustable gastric band 12 relative to the stomach 10 can also occur. The undesirable results of a posterior slip are substantially the same as those described above in conjunction with the slip illustrated in FIG. 2.

Figure 3:
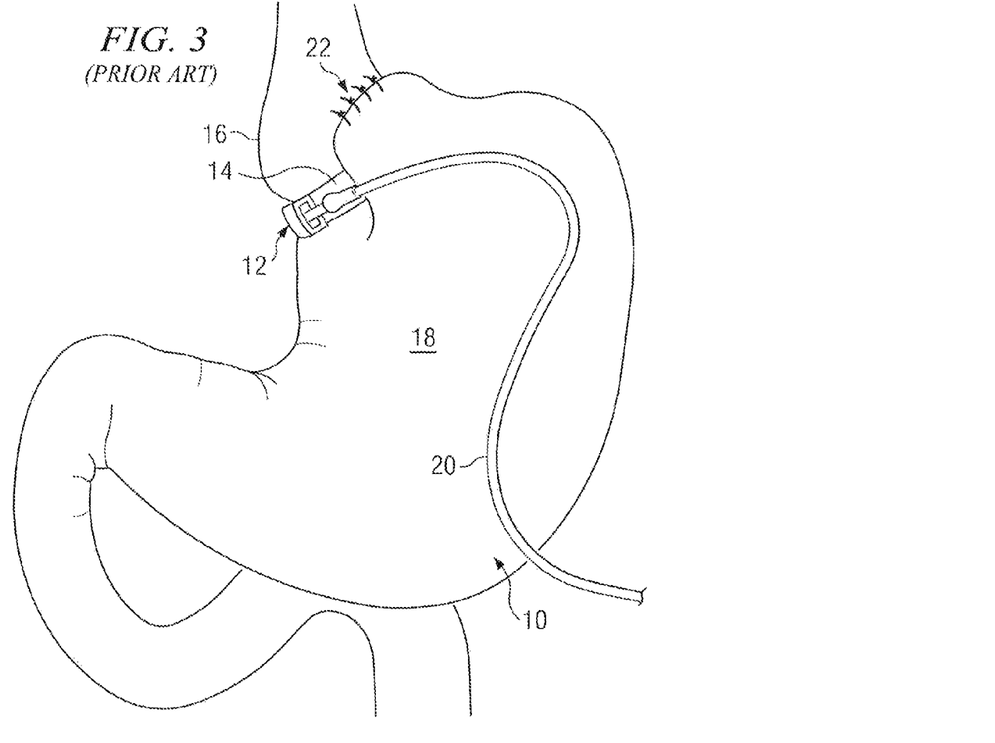
FIG. 3 is an illustration of the use of a stomach flap to secure an adjustable gastric band against movement relative to the stomach.

FIG. 3 illustrates a prior art technique for preventing movement of the adjustable gastric band 12 relative to the stomach 10. A flap comprising part of the lower portion 18 of the stomach 10 is secured to the upper portion 16 by a plurality of sutures 22. So long as the flap remains sutured to the upper portion 16 of the stomach 10 the adjustable gastric band 12 is secured against significant movement relative to the stomach. However, as is well known to those skilled in the art, various occurrences can cause the flap to become disengaged from the upper portion 16 of the stomach 10. For example, the sutures 22 can simply tear loose. It is also possible that the knots which secure the sutures 22 in place will fail either by becoming untied or due to breakage. It is also possible that the sutures will deteriorate under the action of fluids contained within the stomach 10 and/or within the body cavity.

The present invention comprises a method of and apparatus for preventing movement of an adjustable gastric band relative to the stomach upon which the adjustable gastric is installed. In accordance with the broader aspects of the invention, an adjustable gastric band is positioned on a stomach in the conventional manner and is thereafter sutured to the stomach thereby eliminating the possibility of movement of the adjustable gastric band relative to the stomach.

In accordance with a first embodiment of the invention a plurality of tabs are formed integrally with the flexible, substantially non-extendable layer of an adjustable gastric band and are provided with suture receiving holes to facilitate suturing of the adjustable gastric band to the stomach. In accordance with a second embodiment of the invention, lengths of suture material secured to the flexible, substantially non-extendable outer layer of an adjustable gastric band to facilitate suturing of the adjustable gastric band to the stomach.

In accordance with a third embodiment of the invention, the flexible, substantially non-extendable layer of an adjustable gastric band is provided with a plurality of tabs each having a suture receiving hole formed therein and with a plurality of loops formed from suture material for facilitating suturing of the adjustable gastric band to the stomach. In accordance with a fourth embodiment of the invention a plurality of tabs are secured to the flexible, substantially non-extendable layer of an adjustable gastric band and are provided with suture receiving apertures thereby facilitating suturing of the adjustable gastric band to the stomach. In accordance with a fifth embodiment of the invention a length of fabric is secured to the flexible, substantially non-extendable layer of an adjustable gastric band and is provided with a plurality of apertures extending therethrough for facilitating suturing of the adjustable gastric band to the stomach.

BRIEF DESCRIPTION OF THE DRAWINGS

A more complete understanding of the present invention may be had by reference to the following Detailed Description when taken in connection with the accompanying Drawings, wherein.

DETAILED DESCRIPTION

Figure 4:
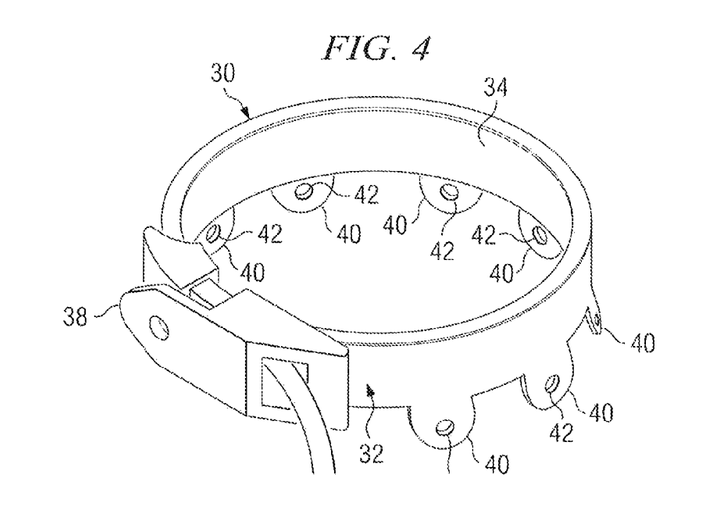
FIG. 4 is a perspective view illustrating a first embodiment of the invention.

Referring now to the drawings, and particularly to FIG. 4 thereof, there is shown an adjustable gastric band 30 comprising a first embodiment of the invention. Although a particular gastric band construction is illustrated in the drawings, those skilled in the art will appreciate that the present invention is applicable to all gastric restrictive devices including but not limited to the Lap Band® adjustable gastric band distributed by INAMDED®, the Swedish Adjustable Gastric Band (SAGB) distributed by Obtech, the MIDBAND adjustable gastric band distributed by Médical Innovation Développement, and the AMI Soft Gastric Band distributed by C.J. Medical.

The adjustable gastric band 30 comprises a flexible, substantially non-extendable outer layer 32 and an inner flexible layer 34. A tube 36 is connected to the inner flexible layer 34 of the adjustable gastric band 30 through a one way valve for use in inflating the flexible layer 34 thereby causing the layer 34 to balloon inwardly. The adjustable gastric band 30 further includes a latching mechanism 38 which is employed to initially secure the adjustable gastric band 30 around the stomach of a patient.

In accordance with the present invention, the flexible, substantially non-extendable layer 32 has a plurality of tabs 40 formed integrally therewith. Each of the tabs 40 has a suture receiving aperture 42 formed therethrough. After the adjustable gastric band 30 has been properly positioned on a stomach and secured in place by the locking mechanism 38, the tabs 40 are utilized to prevent movement of the adjustable gastric band 30 relative to the stomach. This is accomplished by suturing the adjustable gastric band 30 to the stomach utilizing the apertures 42 extending through the tabs 40.

Figures 5, 6:
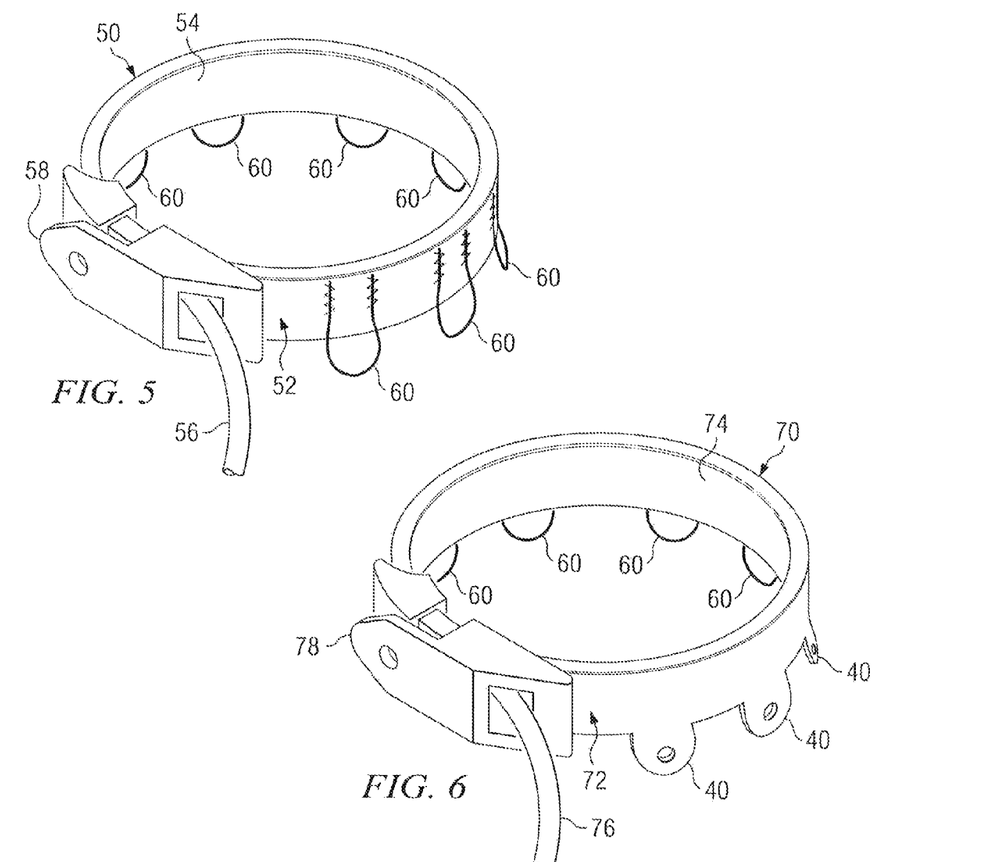
FIG. 5 is a perspective view illustrating a second embodiment of the invention.
FIG. 6 is a perspective view illustrating a third embodiment of the invention.

Referring to FIG. 5, there is shown an adjustable gastric band 50 comprising a second embodiment of the invention. The adjustable gastric band 50 comprises a flexible, substantially non-extendable outer layer 52 and an inner flexible layer 54. A tube 56 is connected to the inner flexible layer 54 of the adjustable gastric band 50 through a one way valve for use in inflating the flexible layer 54 thereby causing the layer 54 to balloon inwardly. The adjustable gastric band 50 further includes a latching mechanism 58 which is employed to initially secure the adjustable gastric band 50 around the stomach of a patient.

In accordance with the present invention, the flexible, substantially non-extendable layer 52 has a plurality of loops 60 secured thereto. Each of the loops 60 comprises a length of suture material which is secured to the outer layer 52 by conventional means such as the use of a suitable adhesive, welding, sewing, stapling, etc. After the adjustable gastric band 50 has been properly positioned on a stomach and secured in place by the locking mechanism 58, the loops 60 are utilized to prevent movement of the adjustable gastric band 50 relative to the stomach. This is accomplished by suturing the adjustable gastric band 50 to the stomach utilizing the loop 60.

Referring to FIG. 6, there is shown an adjustable gastric band 70 comprising a third embodiment of the invention. The adjustable gastric band 70 comprises a flexible, substantially non-extendable outer layer 72 and an inner flexible layer 74. A tube 76 is connected to the inner flexible layer 74 of the adjustable gastric band 70 through a one way valve for use in inflating the flexible layer 74 thereby causing the layer 34 to balloon inwardly. The adjustable gastric band 70 further includes a latching mechanism 78 which is employed to initially secure the adjustable gastric band 70 around the stomach of a patient.

The adjustable gastric band 70 comprises the tabs 40 of the adjustable gastric band 30 of FIG. 4 and the loops 60 of the adjustable gastric band 50 of FIG. 5. It is theorized that the use of the loops 60 on the posterior side of the adjustable gastric band 70 will lessen the drag that would otherwise be experienced in positioning the band 70 around the stomach of a patient.

Figure 7:
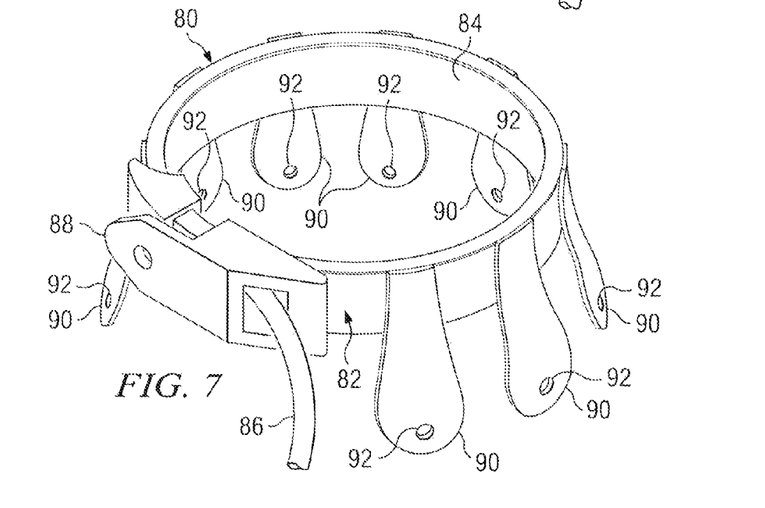
FIG. 7 is perspective view illustrating a fourth embodiment of the invention.

Referring to FIG. 7 thereof, there is shown an adjustable gastric band 80 comprising a fourth embodiment of the invention. The adjustable gastric band 80 comprises a flexible, substantially non-extendable outer layer 82 and an inner flexible layer 84. A tube 86 is connected to the inner flexible layer 84 of the adjustable gastric band 80 through a one way valve for use in inflating the flexible layer 84 thereby causing the layer 84 to balloon inwardly. The adjustable gastric band 80 further includes a latching mechanism 88 which is employed to initially secure the adjustable gastric band 80 around the stomach of a patient.

In accordance with the present invention the flexible, substantially non-extendable layer 32 is provided with a plurality of tabs 90. The tabs 90 are secured to the flexible, substantially non-extendable outer layer of the adjustable gastric band 80 by means of a suitable adhesive, welding, sewing, stapling, etc. Each of the tabs 90 has a suture receiving aperture 92 formed therethrough. After the adjustable gastric band 80 has been properly positioned on a stomach and secured in place by a locking mechanism 88, the tabs 90 are utilized to prevent movement of the adjustable gastric band 80 relative to the stomach. This is accomplished by suturing the adjustable gastric band 80 to the stomach utilizing the apertures 92 extending through the tabs 90.

Figure 8:
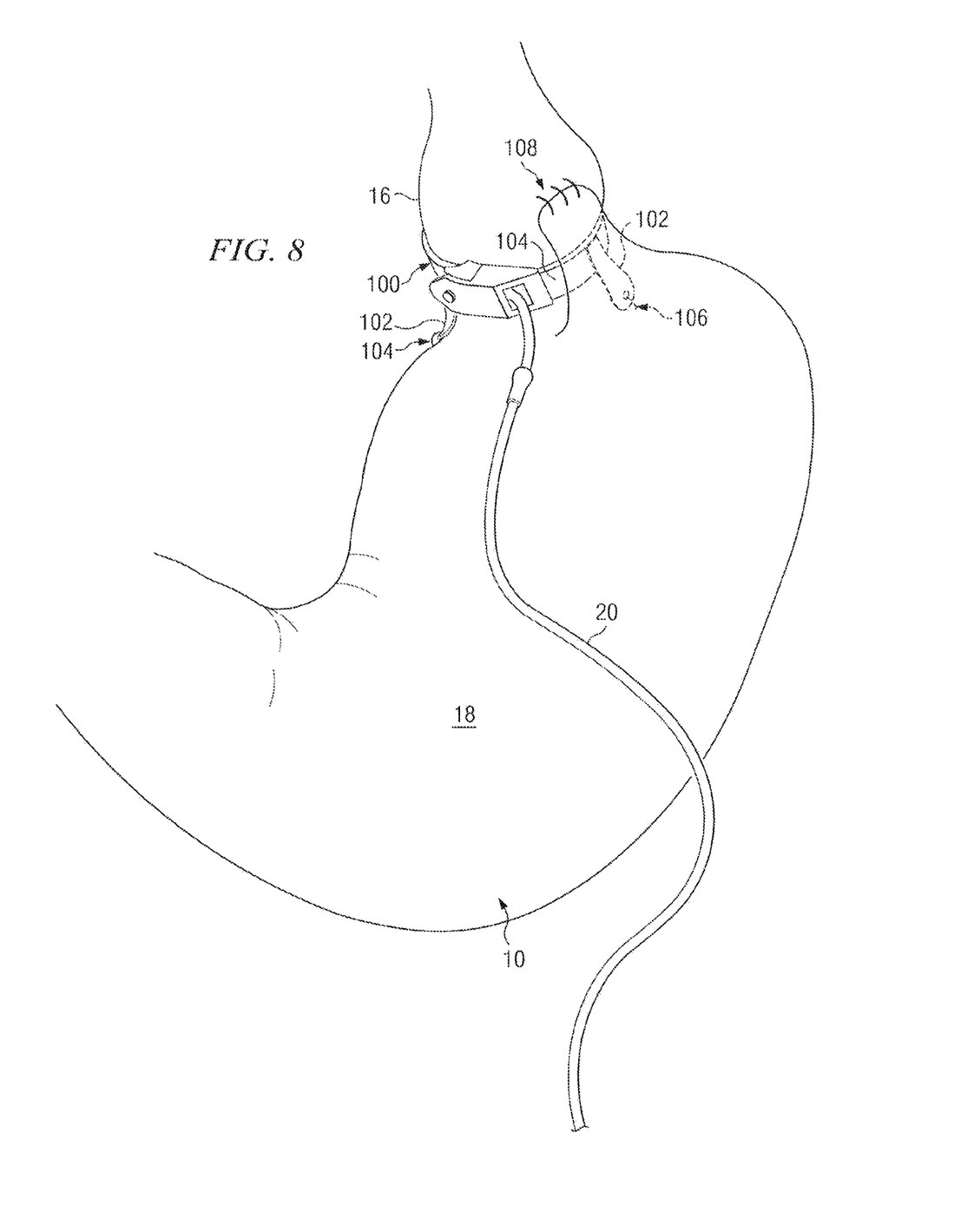
FIG. 8 is perspective view illustrating the use of the first, second, third, and fourth embodiments of the invention in conjunction with a stomach.

FIG. 8 illustrates the utilization of the embodiments of the invention shown in FIGS. 4, 5, 6, and 7 and described hereinabove in conjunction therewith. After the adjustable gastric band 100 is secured around the stomach 10, it is secured in place by means of tabs or loops 102 secured to the flexible, substantially non-extendable outer layer 104 of the adjustable gastric band 100 and sutures 106 which secure the bands or loops 102 to the wall of the stomach 10. Subsequently a flap comprising part of the lower portion 18 of the stomach 10 may be secured to the upper portion 16 thereof utilizing sutures 108. Use of the present invention provides an added safeguard against slippage of the adjustable gastric band 100 in the event that the flap becomes disengaged from the upper portion 16 of the stomach 10 for any reason.

Figure 9:
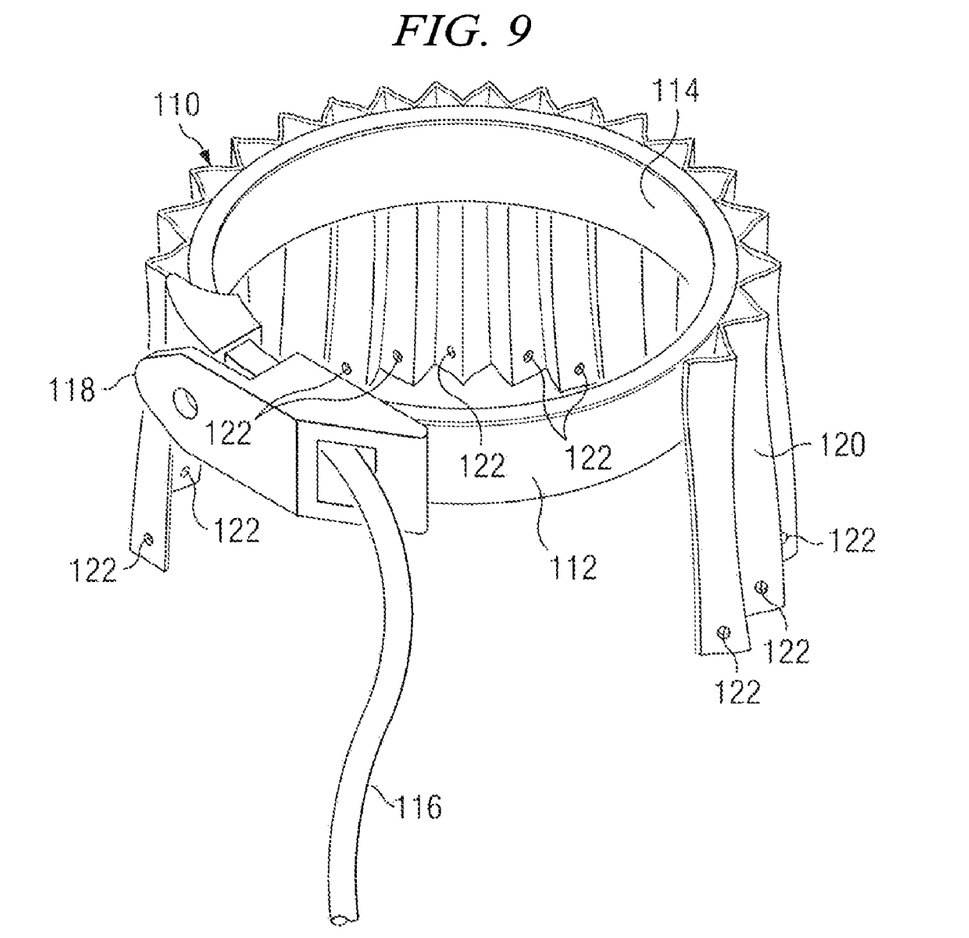
FIG. 9 is perspective view illustrating a fifth embodiment of the invention.

Referring to FIG. 9, there is shown an adjustable gastric band 110 comprising a fifth embodiment of the invention. The adjustable gastric band 110 comprises a flexible, substantially non-extendable outer layer 112 and an inner flexible layer 114. A tube 116 is connected to the inner flexible layer 114 of the adjustable gastric band 110 through a valve for use in inflating the flexible layer 114 thereby causing the layer 114 to balloon outwardly. The adjustable gastric band 110 further includes a latching mechanism 118 which is employed to initially secure the adjustable gastric band 110 around the stomach of a patient.

In accordance with the present invention a fabric layer 120 is secured to the flexible, substantially non-extendable layer 112 of the adjustable gastric band 110. The layer 120 is preferably pleated as illustrated in FIG. 9. The layer 120 may be secured to the flexible, substantially non-extendable layer 112 by any of a variety of conventional techniques such as utilizing a suitable adhesive, welding, sewing, stapling, etc. A plurality of suture receiving aperture 122 extend through the layer 120 adjacent the lower edge thereof.

Figure 10:
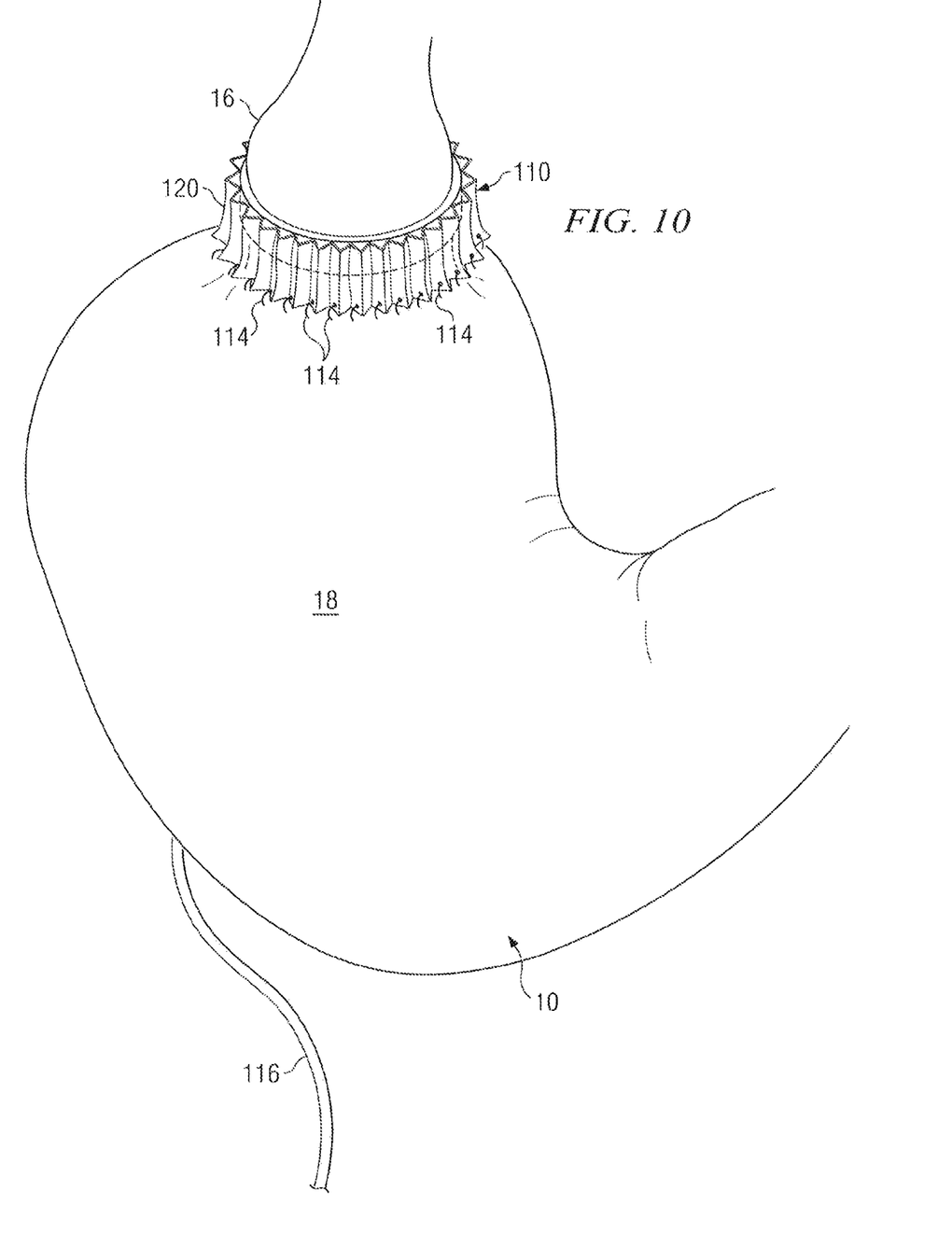
FIG. 10 is perspective view illustrating the use of a fifth embodiment of the invention in conjunction with a stomach.

FIG. 10 illustrates the utilization of the embodiment of the invention shown in FIG. 9 and described hereinabove in conjunction therewith. After the adjustable gastric band is secured around the stomach 10 it is secured in place by means of the layer 120 and sutures 124 and into engagement with the stomach wall to secure the adjustable gastric band 110 against movement relative to the stomach 10.

Although preferred embodiments of the invention have been illustrated in the accompanying Drawings and described in the foregoing Detailed Description, it will be understood that the invention is not limited to the embodiments disclosed, but is capable of numerous rearrangements, modifications, and substitutions of parts and elements without departing from the spirit of the invention.

The invention claimed is:

1. In combination with an adjustable gastric band of the type comprising an outer substantially non-extendable layer and an inner expandable layer for encircling a human stomach and thereafter restricting the passage of food through the stomach, the improvement comprising means for facilitating suturing the adjustable gastric band to the stomach and thereby preventing movement of the adjustable gastric band relative to the stomach;

the means for facilitating suturing of the adjustable gastric band to the stomach comprising a plurality of lengths of suture material each comprising a loop characterized by first and second ends and means for securing the first and second ends of each length of suture material to the outer substantially non-extendable layer of the adjustable gastric band.

2. In combination with an adjustable gastric band of the type comprising an outer substantially non-extendable layer and an inner expandable layer for encircling a human stomach and thereafter restricting the passage of food through the stomach, the improvement comprising means for facilitating suturing the adjustable gastric band to the stomach and thereby preventing movement of the adjustable gastric band relative to the stomach;

the means for facilitating suturing of the adjustable gastric band to the stomach comprising a layer secured to the outer substantially non-extendable layer and extending substantially the entire length thereof and having a plurality of suture receiving apertures formed therethrough.

3. An adjustable gastric band comprising:
an outer substantially non-extendable layer;
an inner expandable member secured to the outer substantially non-extendable layer;
means for securing the outer substantially non-extendable layer and the inner expandable around a human stomach;
means for thereafter inflating the inner expandable member and thereby restricting the passage of food through the stomach;
means for facilitating suturing of the outer substantially non-extendable layer to the stomach and thereby preventing movement of the adjustable gastric band relative to the stomach;
means for facilitating suturing of the adjustable gastric band to the stomach comprising a plurality of lengths of suture material each comprising a loop characterized by first and second ends and means for securing the first and second ends of each length of suture material to the outer substantially non-extendable layer of the adjustable gastric band.

4. An adjustable gastric band comprising:
an outer substantially non-extendable layer;
an inner expandable member secured to the outer substantially non-extendable layer;
means for securing the outer substantially non-extendable layer and the inner expandable around a human stomach;
means for thereafter inflating the inner expandable member and thereby restricting the passage of food through the stomach;
means for facilitating suturing of the outer substantially non-extendable layer to the stomach and thereby preventing movement of the adjustable gastric band relative to the stomach;
the means for facilitating suturing the adjustable gastric band to the stomach comprising a layer extending substantially the entire length of the outer substantially non-extendable layer of the adjustable gastric band and having a plurality of suture receiving apertures formed therethrough.

5. A method of gastric banding comprising the steps of:
providing an outer substantially non-extendable layer;
providing an inner expandable member;
securing the inner expandable member to the outer substantially non-extendable layer;
extending the outer substantially non-extendable layer and the inner expandable member around a human stomach;
securing the opposed ends of the outer substantially non-extendable layer one to another;
suturing the substantially non-extendable layer to the stomach and thereby preventing relative movement between the gastric band and the stomach;
thereafter inflating the inner expandable member and thereby restricting the passage of food through the stomach;
the step of suturing the adjustable gastric band to the stomach comprising a plurality of tabs each non-integrally secured to the outer substantially non-extendable layer of the adjustable gastric band and each having a suture receiving aperture formed therethrough and extending sutures through the suture receiving aperture and an adjacent area of the stomach.

6. A method of gastric banding comprising the steps of:
providing an outer substantially non-extendable layer;
providing an inner expandable member;
securing the inner expandable member to the outer substantially non-extendable layer;
extending the outer substantially non-extendable layer and the inner expandable member around a human stomach;
securing the opposed ends of the outer substantially non-extendable layer one to another;
suturing the substantially non-extendable layer to the stomach and thereby preventing relative movement between the gastric band and the stomach;
thereafter inflating the inner expandable member and thereby restricting the passage of food through the stomach and;
wherein the steps of suturing of the adjustable gastric band to the stomach comprising a plurality of lengths of suture material each comprising a loop characterized by first and second ends and securing the first and second ends of each length of suture material to the outer substantially non-extendable layer of the adjustable gastric band and extending sutures through each of the loops and an adjacent area of the stomach.

7. A method of gastric banding comprising the steps of:
providing an outer substantially non-extendable layer;
providing an inner expandable member;
securing the inner expandable member to the outer substantially non-extendable layer;
extending the outer substantially non-extendable layer and the inner expandable member around a human stomach;
securing the opposed ends of the outer substantially non-extendable layer one to another;
suturing the substantially non-extendable layer to the stomach and thereby preventing relative movement between the gastric band and the stomach;
thereafter inflating the inner expandable member and thereby restricting the passage of food through the stomach;
wherein the step of suturing the adjustable gastric band to the stomach comprising a layer having a plurality of suture receiving apertures formed therethrough and securing the layer to the outer substantially non-extendable layer and extending sutures through the suture receiving aperture and an adjacent area of the stomach.

* * * * *